United States Patent [19]

Bruzzese et al.

[11] Patent Number: 4,599,406
[45] Date of Patent: Jul. 8, 1986

[54] PROCESS FOR PREPARING 2-METHYL-N-(2-PYRIDYL)-2H-1,2-BENZO-THIAZINE-3-CARBOXAMIDE 1,1-DIOXIDE DERIVATIVES AND INTERMEDIATES THEREFOR

[75] Inventors: Tiberio Bruzzese; Ernani Dell'Acqua, both of Milan; Franco Ottoni, Cesano Boscone; Holger H. van den Heuvel, Milan, all of Italy

[73] Assignee: SPA-Societa Prodotti Antibiotici spa, Milan, Italy

[21] Appl. No.: 681,186

[22] Filed: Dec. 13, 1984

[30] Foreign Application Priority Data

Dec. 16, 1983 [IT] Italy ................................ 24214 A

[51] Int. Cl.$^4$ ................................ C07D 279/02
[52] U.S. Cl. ................................................ 544/49
[58] Field of Search .................................... 544/49

[56] References Cited

U.S. PATENT DOCUMENTS

| | | | |
|---|---|---|---|
| 3,960,856 | 6/1976 | Genzer et al. | 544/49 |
| 4,100,347 | 7/1978 | Hammen | 544/49 |
| 4,309,427 | 1/1982 | Lombardino | 544/49 |
| 4,461,768 | 7/1984 | Dell'Acqua et al. | 544/49 |

FOREIGN PATENT DOCUMENTS 0070888  5/1982  Japan ................................ 544/49

OTHER PUBLICATIONS

Morrison et al., "Organic Chemistry Textbook", Allyn and Bacon, Inc., 1978, pp. 675, 793.

Primary Examiner—Henry R. Jiles
Assistant Examiner—J. G. Mullins
Attorney, Agent, or Firm—Oblon, Fisher, Spivak, McClelland & Maier

[57] ABSTRACT

The process for the preparation of derivatives of 2-methyl-N-(2-pyridyl)-2H-1,2-benzothiazine-3-carboxamide 1,1-dioxide of the formula

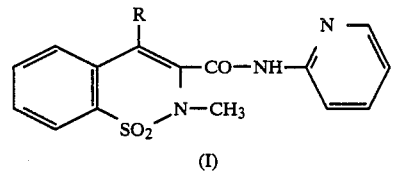

(I)

$\begin{cases} \text{Ia, R} = \text{OH} \\ \text{Ib, R} = \text{OR}_1; \text{R}_1 = \text{CO}-\text{CH}=\text{CH}-\text{C}_6\text{H}_5 \end{cases}$ wherein R represents hydroxy (Ia) or substituted hydroxy $OR_1$ in which $R_1$ is the cinnamoyl radical $-CO-CH=CH-C_6H_5$ (Ib) consists in reacting a strong base salt of 4-hydroxy-2-methyl-2H-1,2-benzothiazine-3-carboxylic acid 1,1-dioxide with an acyl chloride $R_1Cl$, in which $R_1$ is the cinnamoyl radical, or $R_2Cl$, in which $R_2$ is an aromatic or aliphatic $C_2$–$C_6$ acyl radical to give the corresponding mixed anhydride, optionally esterified at position 4, which is then reacted with 2-aminopyridine to give the desired amide.

14 Claims, No Drawings

PROCESS FOR PREPARING 2-METHYL-N-(2-PYRIDYL)-2H-1,2-BENZOTHIAZINE-3-CARBOXAMIDE 1,1-DIOXIDE DERIVATIVES AND INTERMEDIATES THEREFOR

The present invention is concerned with a new process for preparing benzothiazine compounds of the formula

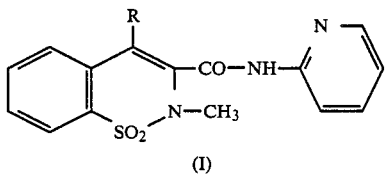

(I)

{ Ia, R = OH
  Ib, R = OR₁; R₁ = CO—CH=CH—C₆H₅ } wherein R represents hydroxy OH (Ia) or substituted hydroxy OR₁ in which R₁ is the cinnamoyl radical (Ib). These compounds are known in the art. For instance, 4-hydroxy-2-methyl-N-(2-pyridyl)-2H-1,2-benzothiazine-3-carboxamide 1,1-dioxide (Ia, generic name piroxicam) is reported in several papers (see e.g. J. G. Lombardino et al., J. Med. Chem. 16, 493, 1973) and patents (see e.g. U.S. Pat. No. 3,591,584). 4-Cinnamoyloxy-2-methyl-N-(2-pyridyl)-2H-1,2-benzothiazine-3-carboxamide 1,1-dioxide is described in Italian patent application No. 24993 A/81 filed by us. Both products are endowed with a high therapeutical activity as non steroidal anti-inflammatory drugs.

A typical process for preparing Ia is reported in U.S. Pat. No. 3,591,584. It consists, for instance, in reacting 4-hydroxy-2-methyl-2H-1,2-benzothiazine-3-carboxylic acid methyl ester 1,1-dioxide (II) with 2-aminopyridine (2-AP) under drastic conditions, i.e. in xylene under reflux for prolonged periods of time; the yield is 45%. (J. G. Lombardino et al., J. Med. Chem.16, 493, 1973).

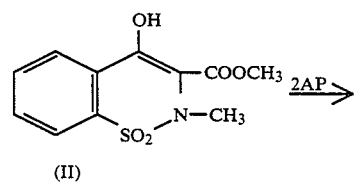

(II)

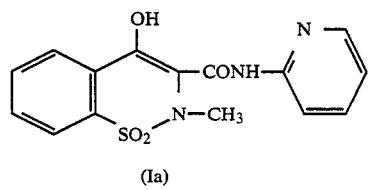

(Ia)

The ester II used as reactant may be obtained in turn, for instance, through a process comprising rearrangement of 3-oxo-1,2-benzoiso-thiazoline-2-acetic acid methyl ester 1,1-dioxide (III) (saccharine-2-acetic acid methyl ester) to 4-hydroxy-2H-1,2-benzothiazine-3-carboxylic acid ester 1,1-dioxide (IV) by the action of sodium methoxide followed by 2-alkylation with methyl iodide.

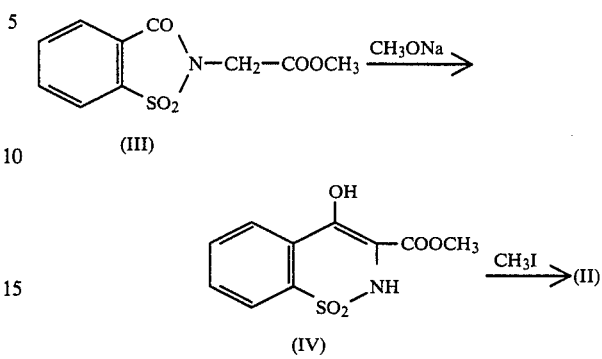

U.S. Pat. No. 3,892,740 describes a process for preparing Ia starting from a 4-alkoxy, preferably 4-isopropoxy-2-methyl-2H-1,2-benzothiazine-3-carboxylic acid 1,1-dioxide (V), which is reacted with amines (e.g. 2-aminopyridine) in the presence of a condensation agent such as N-ethoxycarbonyl-2-ethoxy-1,2-dihydroquinoline (EEDQ). The obtained amide (VI) is then treated with hydrobromic acid to split the ether group at position 4 and obtain a.o. compound Ia

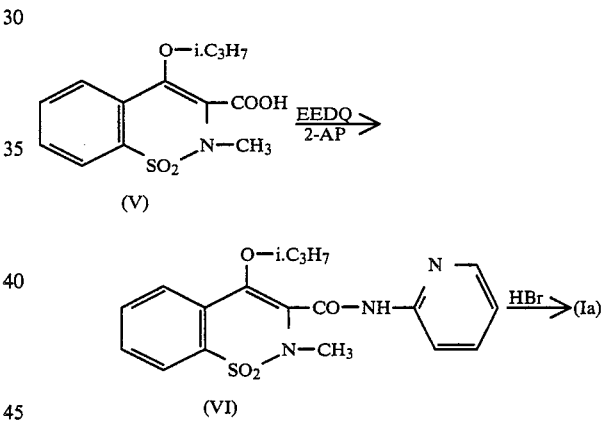

Attempts to find a more direct route starting from the 4-hydroxy-derivative of V, i.e. from the acid VII not protected by the ether group failed inasmuch this acid was actually prepared by hydrolysis of the corresponding ester II, but was too unstable to be of practical use. As a matter of fact, through a tautomeric form it shows a beta-ketoacid structure (U.S. Pat. No. 3,892,740, lines 24-27, column 4) which causes rapid decarboxylation as soon as it forms. Such instability was confirmed by J. G. Lombardino and H. A. Watson Jr. in J. Heterocyclic Chem. 13, 333, 1976.

It is to be noted, however, that on a data subsequent to U.S. Pat. No. 3,892,740 and to the above quoted paper, U.S. Pat. No. 4,100,347 of July 11, 1978 reports preparation of 4-hydroxy-2-methyl-2H-1,2-benzothiazine-3-carboxylic acid 1,1-dioxide (VII) claiming the product as far as produced in crystalline form, and also describes the obtainment of the desired end amide (Ia) starting from that intermediate.

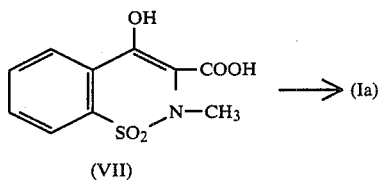

(VII)

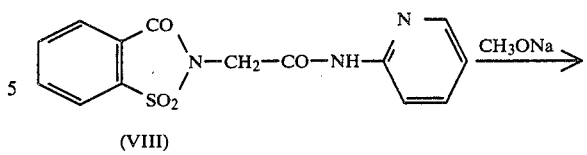

(VIII)

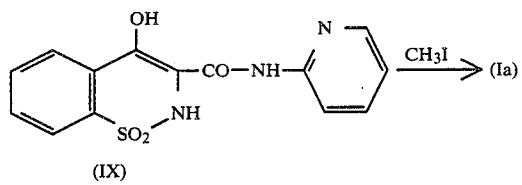

(IX)

More particularly, the end step of the process consists in reacting with 2-aminopyridine the chloride of the acid VII (yield in Ia, 79% of crude product which in turn gives 30% of pure product), or the acid itself in the presence of a condensation agent such as N-ethoxycarbonyl-2-ethoxy-1,2-dihydroquinoline (EEDQ) (no yield is given, the product is detected by thin layer chromatography, or the mixed anhydride of the acid with alcoxycarbonic or benzyloxycarbonic acids (no examples are given).

The preparation of the acid VII used as a reactant is carried out by alkaline hydrolysis of the corresponding alkyl $C_1$–$C_{12}$ or phenylalkyl ($C_1$–$C_3$ alkyl) esters followed by acidification to pH 0–5.5. This hydrolysis is carried out in aqueous (maximum yield 34.6%) or non-aqueous medium, in the latter case by working in the presence of 'crown ethers' (macrocyclic ethers) of which the solubilizing effect on alkali metal hydroxides is known; and in solvents like benzene or toluene under reflux for 50 hours (yield 61.9%).

A further method for preparing Ia is described in U.S. Pat. No. 4,074,048. By this method, N-(2-pyridyl)-2,3-dihydro-3-oxo-1,2-benzoisothiazoline-2-acetamide (VIII) is subjected to sodium methoxide catalized rearrangement to 4-hydroxy-N-(2-pyridyl)-2H-1,2-benzothiazine-3-carboxamide 1,1-dioxide (IX) followed by methylation at position 2 with methyl iodide to give Ia.

Finally, a typical preparation method for Ib is described in Italian patent application No. 24993 A/81 and consists in reacting N-(2-pyridyl)-2-methyl-4-hydroxy-2H-1,2-benzothiazine-3-carboxamide 1,1-dioxide (Ia) with cinnamic acid or a reactive functional derivative of the same, such as cinnamoyl chloride, to give the desired ester at position 4 (Ib).

We have now discovered a new process for the preparation of benzothiazine compounds of formula I, which comprises reacting a strong base salt (X), such as the sodium salt, of 4-hydroxy-2-methyl-2H-1,2-benzothiazine-3-carboxylic acid 1,1-dioxide (IX) with an acyl chloride $R_1Cl$, wherein $R_1$ is the cinnamoyl radical, or $R_2Cl$, wherein $R_2$ is an aromatic or aliphatic ($C_2$–$C_6$) acyl radical to give the corresponding mixed anhydride (XI), optionally esterified at position 4, and reacting the obtained mixed anhydrides (XI) or (XII) with 2-aminopyridine (2-AP) to give the desired amide Ia or Ib.

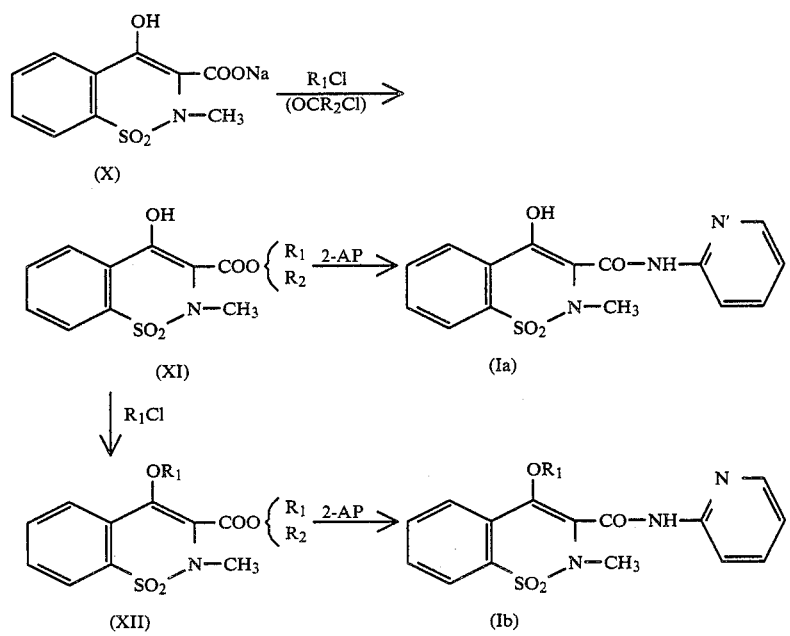

In a more detailed description of the process, the first reaction step starting from the sodium salt (X) or other salts with strong bases is preferably carried out by using cinnamoyl chloride in an about equimolecular amount to give the mixed anhydride XI. However, also other organic acid halogenides, such as an aromatic acid chloride, e.g. benzoic acid chloride, or an aliphatic acid chloride, e.g. pivalic or acetic acid chloride, may be advantageously employed. If desired, the obtained anhydride XI may be subjected, preferably in situ, to a further acylation process at position 4 with cinnamoyl chloride in a moderate excess to give the ester-anhydride XII. Obviously, if the first reaction step giving XI is carried out with cinnamoyl chloride R₁Cl, then the whole process is advantageously carried out in a single step by directly reacting the sodium salt X or, preferably, the disodium salt (carboxylate-enolate)

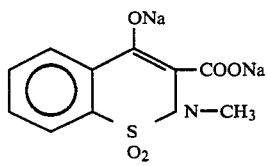

with an amount of cinnamoyl chloride more than the double of the stoichiometric amount, usually 2-3 times the molar ratio, thus directly obtaining the product XII.

In all cases the acylation reaction proceeds smoothly by working in an inert solvent such as e.g. methylene chloride, and under very mild reaction conditions, usually at a temperature ranging between 0° C. and the boiling temperature of the solvent and for a time comprised between about 10 and about 90 minutes. Recovery of the products is effected through conventional procedures, and very high yields and high purity products are normally obtained.

The subsequent amidation reaction starting from anhydrides XI or XII is also carried out by a very simple procedure, i.e. by treatment with 2-aminopyridine preferably in two stoichiometric amounts in order to neutralize acidity deriving from anhydride splitting. It is to be noted that anhydrides of structure XI are advantageously reacted without previous isolation and/or purification, being of poor stability to chemical treatment in view of their high reactivity.

On the contrary, anhydrides XII may be previously isolated, inasmuch their stability seems to be markedly improved by the 4-esterification and the subsequent structural adjustement in the tautomeric enol form.

It is also pointed out that aminolysis of the mixed anhydrides XI and XII always proceeds, regardless of their structure with reference to radicals R₁ and R₂ and the adopted reaction conditions, towards the desired formation of amides Ia and Ib respectively with liberation of acids R₁OH and R₂OH. On the contrary it is well known in the art that aminolysis of mixed anhydrides may proceed towards two different pathways depending on the way of opening of the bonds C—O—C, to give alternatively, in the above considered case, the amides R₁-2AP and R₂-2AP.

Just like the former reaction step, amidation also is profitably carried out in an inert solvent such as methylene chloride at moderate temperatures within the range of 0° C. to about 40° C., usually 15°-20° C., and for reaction periods of about 1-3 hours.

Recovery of the product is carried out by conventional procedures such as e.g., by precipitation with diethyl ether. If the starting anhydride is XII, it is advantageous to directly use a reaction solvent composed of methylene chloride: diethyl ether in a ratio of about 1:4, thus causing precipitation of the reaction product and preventing or limiting every possible hydrolytic splitting of the 4-ester group.

Yield and purity of products Ia and Ib are very satisfactory. For instance, Ia is obtained starting from X in a single step, without adopting the drastic reaction conditions reported in the art and in higher yields, ranging between 60-80% (see J. G. Lombardino et al. J. Med. Chem. 16, 493, 1973, who report a 45% yield).

As to the salts of 4-hydroxy-2-methyl-2H-1,2,benzothiazine-3-carboxylic acid 1,1-dioxide, such as the sodium (X), disodium (XIII) and other salts used as intermediates in the present invention, they are easily prepared starting from easily available compounds. For instance, by working according to known synthetic methods or their obvious modification (H. Eckenroth and G. Koerppen, Chem. Ber. 30, 1265, 1897; U.S. Pat. No. 4,074,048; etc.) it is possible to prepare both the known alkyl esters and a series of new esters of 3-oxo-1,2-benzoisothiazolin-2-acetic acid 1,1-dioxide of the following structure (XIV):

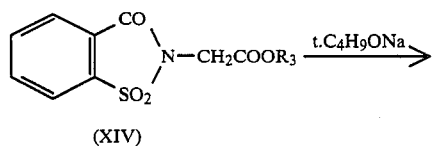

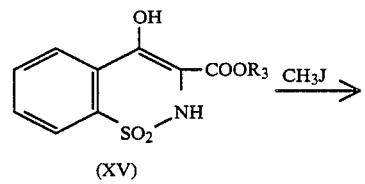

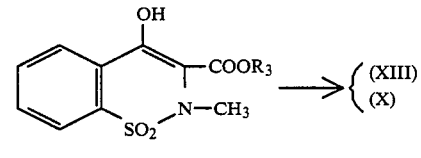

wherein R₃ represents a hydroxyalkyl group C₂-C₆ or a cycloalkyl group C₃-C₆.

Compounds XIV are then subjected to rearrangement by known procedures (K. Abe et al., Yakugaku Zasshi 76, 1058, 1956; U.S. Pat. Nos. 3,284,450; 3,501,466; 3,591,584; H. Zinnes et al., J. Org. Chem. 30, 2241, 1965; etc.) and their obvious modifications, through catalysis induced by alkali metal alcoxides, preferably sodium or potassium ter-butoxide, who are able to prevent transesterification which is somethimes observed on radical R₃. The thus obtained esters of 4-hydroxy-2H-1,2-benzothiazine-3-carboxylic acid 1,1-dioxide of structure XV, are in turn treated with methyl iodide to give the methyl derivatives XVI, in which R₃ preserves the above indicated meaning. The thus obtained compounds XV and XVI are new.

It has been noted that the foregoing products of formula XVI may be easily hydrolized with alcali metal hydroxides in an alkanol, preferably with sodium hydroxide in ethanol, by a short heating to the boiling temperature (about 1-2 hours) to give the disodium salt XIII of 4-hydroxy-2-methyl-2H-1,2-benzothiazine-3-carboxylic acid 1,1-dioxide in almost quantitative yields. Compound XIII, having the carboxy group blocked as a salt, is entirely stable, contrary to what is reported in the art for the corresponding acid VII, and may be converted by obvious procedures into the monosodium salt X or other strong base salts to be used, if preferred, as intermediates in the process of the present invention.

Use of compounds XIV, XV and XVI is a substantial feature of our new process for preparing coumpounds of formula I. In some instances, this use represents an improvement in comparison with other compounds known in the art, such as use of those in which $R_3$ is methyl or ethyl. For instance, hydroxyethyl (XIV, $R_3 = -CH_2CH_2OH$) and cyclohexyl (XIV, $R_3 = -C_6H_{11}$) esters of 3-oxo-1,2-benzoisothiazoline-2-acetic acid 1,1-dioxide may be easily obtained in high yields by an esterification procedure involving use of, respectively, ethylene glycol or cyclohexanol, these latter reactants being easily available and unexpensive. Also the subsequent rearrangement to compounds XV is easily carried out, still working, if desired, in the presence of the corresponding alkanols as the solvents, and getting high yields.

In conclusion, the high yields obtained in the alkaline hydrolysis step to give XIII and the mild reaction condition which were found by us to be sufficient to complete the hydrolysis, are surprising and represent an advance in technology represented, for instance, by U.S. Pat. No. 4,100,347. As above stated, this Patent reports maximum alkaline hydrolysis yields of 34.6% in aqueous medium and 61.9% in benzene or toluene after refluxing for 50 hours.

The following examples of preparation of intermediate and end compounds of the present invention are given by way of illustration only but are not intended as limiting the scope of the invention.

EXAMPLE 1

To a solution of 20.2 g (0.2 mole) of triethylamine in 60 ml of ethyleneglycol, 22.6 g (0.2 mole) of chloroacetyl chloride are added dropwise while cooling at 10° C. The temperature is then allowed to rise to room temperature, then 300 ml of acetone are added, followed by 300 ml of diethyl ether. After short stirring the precipitate of triethylamine hydrochloride is filtered off and the filtrate evaporated under reduced pressure. The residue (65 g), an ethylene glycol solution of 2-hydroxyethyl chloroacetate, may be further distilled to give the desired ester in pure form, but is profitably used as such in the subsequent reaction. Thus, 30.8 g (0.15 mole) of saccharine sodium salt are added and the mixture is heated at 120° C. for 2 hours with stirring. After cooling the reaction mixture is poured into 300 ml of cold water.

The precipitate is collected, treated with benzene and dried to give 34 g (yield 79.4%) of substantially pure 2-hydroxyethyl 3-oxo-1,2-benzoisothiazoline-2-acetate 1,1-dioxide, m.p. 125°-126° C., Rf 0.78 (thin layer chromatography (TLC) on silicagel 60 Merck F 254, eluent methylene chloride: methanol 94:6).

Anal. for $C_{11}H_{11}NO_6S$: calc. %: C 46.31, H 3.89, N 4.91, S 11.24, found %: C 46.82, H 3.91, N 4.87, S 11.20.

EXAMPLE 2

A solution of 14 g (0.14 mole) of cyclohexanol and 19.4 g (0.14 mole) of triethylamine in 140 ml of methylene chloride is cooled at 4° C., then 15.7 g (0.13 mole) of chloracetyl chloride in 70 ml of methylene chloride are quickly dropped in. The mixture is stirred for 20 minutes at room temperature, then the solution is thoroughly washed with water, dried over sodium sulfate and evaporated to dryness under reduced pressure to give 17.6 g (yield 76.6%) of an oily residue of cyclohexyl chloroacetate.

This product may be purified by distillation but it is advantageously used as such in the subsequent reaction step by adding it with stirring to a solution of 20.5 g (0.1 mole) of saccharine sodium salt in 15 ml of dimethylformamide. The reaction mixture is heated to 120° for 5 hours, then it is cooled and poured with stirring into 500 ml of water. The sticky precipitate is extracted with methylene chloride, the organic solution is dried over sodium sulfate and evaporated to dryness. The residue is crystallized from 150 ml of diethyl ether and 200 ml of petroleum ether, giving 21 g of cyclohexyl 3-oxo-1,2-benzoisothiazoline-2-acetate 1,1-dioxide, m.p. 83° C., yield 65%—Rf 0.50 (TLC on silicagel 60 Merck F 254, eluent methylene chloride).

Anal. for $C_{15}H_{17}NO_5S$: calc. %: C 55.71, H 5.30, N 4.33, S 9.91, found %: C 55.87, H 5.32, N 4.30, S 9.95.

EXAMPLE 3

To a mixture, cooled at 18° C., of 19 g (0.17 mole) of potassium tert-butoxide in 100 ml of dimethylsulfoxide, 13.2 g (0.046 mole) of 2-hydroxyethyl 3-oxo-1,2-benzoisothiazoline-2-acetate 1,1-dioxide prepared in Example 1 are slowly added. The mixture is stirred for 10 minutes at room temperature and then rapidly dropped into 700 ml of 10% hydrochloric acid while cooling externally to 0°-5° C. The precipitate is kept under stirring at this temperature for 1-2 hours, then it is collected and washed with methylene chloride to give, after drying, 8.8 g (yield 67%) of 2-hydroxyethyl 4-hydroxy-2H-1,2-benzothiazine-3-carboxylate 1,1-dioxide, m.p. 158°-159° C., Rf 0.57 (TLC as in Example 1).

If desired, the compound may be further purified by column chromatography on silicagel, eluent methylene chloride: methanol 98:2.

Analysis for $C_{11}H_{11}NO_6S$: calc. %: C 46.31 H 3.89 N 4.91 S 11.24, found %: C 46.28 H 3.91 N 4.90 S 11.15.

EXAMPLE 4

1.53 g (0.066 gram -atoms) of sodium metal are treated for 30 minuted at 110° C. with 75 ml of cyclohexanol to give the corresponding alcoxide, the 5 g (0.015 mole) of cyclohexyl 3-oxo-1,2-benzoisothiazoline-2-acetate 1,1-dioxide, obtained according to Example 2, are added while keeping the same temperature.

The reaction mixture, which initially becomes more fluid, is kept under stirring at 110° C. for 1 hour, which causes formation of a more dense mass. After cooling, the mixture is diluted with 75 ml of dimethylacetamide and poured into an excess of 10% hydrochloric acid. The supernatant oily layer is extracted with methylene chloride and the organic solution is washed thoroughly with water to eliminate residual cyclohexanol. After drying over sodium sulfate and almost complete evaporation of the solvent, the residue is treated with 1-2 volumes of n-hexane and allowed to crystallize by standing at low temperature. Yield 2.5 g (50%) of cyclohexyl 4-hydroxy-2H-1,2-benzothiazine-3-carboxylate 1,1-dioxide, m.p. 158° C., Rf 0.54 (TLC as in Example 2).

For analytical purposes the product may be further purified by solution in 10 parts of diethyl ether followed by slow precipitation by the addition of the same volume of n-hexane and subsequent short standing at room temperature.

Analysis for $C_{15}H_{17}NO_5S$: calc. %: C 55.71, H 5.30, N 4.33, S 9.91, found %: C 55.60, H 5.38, N 4.33, S 9.84.

EXAMPLE 5

To a mixture of 5 ml of water, 125 ml of ethanol and 73 ml (0.073 mole) of N sodium hydroxide, 10 g (0.035 mole) of 2-hydroxyethyl 4-hydroxy-2H-1,2-benzothiazine-3-carboxylate 1,1 dioxide (obtained as described in Example 3) are added followed, after complete solution, by 10.4 g (0.073 mole) of methyl iodide. The mixture is stirred at room temperature for 1.5 hours, then 10% hydrochloric acid is added to pH 1.5 and the mixture is evaporated under reduced pressure to one half its volume, thus removing practically all the ethanol. After cooling the precipitated solid is collected, washed with some cold water and dried at 40° C. in vacuo. Yield 9.4 g (89.7%) of 2-hydroxyethyl 4-hydroxy-2-methyl-2H-1,2-benzothiazine-3-carboxylate 1,1-dioxide, m.p. 122°-123° C.

Rf 0.80 (TLC as in Example 1).

Analysis for $C_{12}H_{13}NO_6S$: calc. %: C 48.16, H 4,38, N 4.68, S 10.71, found %: C 47.90, H 4.39, N 4.65, S 10.75.

EXAMPLE 6

To a mixture of 74 ml (0.074 mole) of N sodium hydroxide, 55 ml of water and 125 ml of ethanol, 12 g (0.037 mole) of cyclohexyl 4-hydroxy-2H-1,2-benzothiazine-3-carboxylate 1,1-dioxide (obtained as in Example 4) are added, followed, with stirring, by 10.5 g (0.074 mole) of methyl iodide.

The reaction mixture is kept at room temperature for 2 hours, then hydrochloric acid is added to pH 1 and the solution is evaporated almost to dryness. On cooling and standing the oily precipitate becomes solid and is collected by filtration giving 11 g (yield 88%) of cyclohexyl 4-hydroxy-2-methyl-2H-1,2-benzothiazine-3-carboxylate 1,1-dioxide, m.p. 112° C., Rf 0.78 (TLC) (acc. Ex. 2). If desired for analytical purposes the compound may be further purified by crystallization from 10 volumes of a mixture diethyl ether: n-hexane 1:1.

Analysis for $C_{16}H_{19}NO_5S$: calc. %: C 56.96, H 5.68, N 4.15, S 9.50, found %: C 57.23, H 5.75, N 4.12, S 9.48.

EXAMPLE 7

Twenty grammes of sodium hydroxide are dissolved in 14 ml of water under moderate external cooling and the solution is diluted with 200 ml of ethanol, then 10 g (0.033 mole) of 2-hydroxyethyl 4-hydroxy-2-methyl-2H-1,2-benzothiazine-3-carboxylate 1,1-dioxide (obtained as in Example 5) are added.

The mixture is refluxed for 1.5 hours then cooled 4° C. and kept at this temperature for 1-2 hours under stirring. The suspended product is collected, washed with anhydrous ethanol and dried at 50° C. in vacuo Yield 9.8 g (98%) of essentially pure disodium salt of 4-hydroxy-2-methyl-2H-1,2-benzothiazine-3-carboxylic acid 1,1-dioxide as a colorless or slightly yellowish crystalline solid.

The product is water soluble and by the addition of acids the corresponding acid precipitates out, but cannot be recovered without at least partial decarboxylation. It is practically insoluble in ethanol and the usual organic solvents.

Analysis for $C_{10}H_7NO_5S$ Na: calc. %: C 50.14, H 2.36, N 4.68, S 10.71, found %: C 40.32, H 2.33, N 4.67, S 10.59, titre (perchloric acid): 98.8%.

EXAMPLE 8

Ten grammes (0.03 mole) of cyclohexyl 4-hydroxy-2-methyl-2H-1,2-benzothiazine-3-carboxylate 1,1-dioxide (prepared as in Example 6) are treated with sodium hydroxide by the same procedure as in Example 7. The disodium salt of 4-hydroxy-2-methyl-2H-1,2-benzothiazine-3-carboxylic acid 1,1-dioxide is obtained in a practically theoretical yield (98%). It is identical to the product of Example 7, as confirmed by the chemical and physical data.

EXAMPLE 9

To a suspension of 6 g (0.02 mole) of disodium salt of 4-hydroxy-2-methyl-2H-1,2-benzothiazine-3-carboxylic acid 1,1-dioxide (prepared as in Examples 7 and 8) in 70 ml of methylene chloride, an equivalent amount of 2N hydrochloric acid (20 ml, 40 meq) is added with stirring and cooling, followed by 2.12 g (0.021 mole) of triethylamine.

The organic phase is separated and dried over sodium sulfate. The solution contains, in a practically quantitative yield, the triethylamine salt of 4-hydroxy-2-methyl-2H-1,2-benzothiazine-3-carboxylic acid 1,1-dioxide, which does not require further purification and is used as such for subsequent reactions.

EXAMPLE 10

In a solution of 10.7 (0.03 mole) of triethylamine salt of 4-hydroxy-2-methyl-2H-1,2-benzothiazine-3-carboxylic acid 1,1-dioxide (from Example 9) in 100 ml of methylene chloride, 5.0 g (0.03 mole) of cinnamoyl chloride are dropped with moderate cooling. The mixture is kept at room temperature under stirring for 10 minutes, then the solution containing the desired mixed anhydride (9.2 g, yield 80%) is directly reacted, by a preferred procedure, according to one of the following Examples. Alternatively, the reaction product is recovered by precipitation with diethyl ether. Crude cinnamoyl anhydride of 4-hydroxy-2-methyl-2H-1,2-benzothiazine-3-carboxylic acid 1,1-dioxide is obtained, which cannot by crystallized from the usual organic solvents owing to its reactivity and poor stability.

Analysis (crude product) for $C_{19}H_{15}NO_6S$: calc. %: C 59.21, H 3.92, N 3.63, S 8.32, found %: C 58.30, H 3.86, N. 3.55, S 8.22.

EXAMPLE 11

By reacting the triethylamine salt of 4-hydroxy-2-methyl-2H-1,2-benzothiazine-3-carboxylic acid 1,1-dioxide with the appropriate acyl chlorides, essentially in agreement with the process of Example 10, the following mixed anhydrides are obtained

|  | Yield % |
|---|---|
| Acetic anhydride | 72 |
| Trimethylacetic anhydride | 65 |
| Benzoic anhydride | 70 |

EXAMPLE 12

To a suspension of 30 g (0.1 mole) of disodium salt of 4-hydroxy-2-methyl-2H-1,2-benzothiazine-3-carboxylic acid 1,1-dioxide in 300 ml of methylene chloride, 41.6 g (0.25 mole) of cinnamoyl chloride are added by keeping the reaction at room temperature. The reaction mixture is stirred for 1.5 hours at about 25°, then the suspended amorphous solid, which is sodium chloride formed during the reaction, is filtered off and the solution is evaporated to a small volume. 300 ml of diethyl ether are then added and the mixture is gently stirred for 2 hours at about 10° C., thus obtaining an abundant crystalline precipitate.

The solid is collected, washed with diethyl ether and dried at 40° C. in vacuo. Yield 36.1 g (70%) of cinnamoyl anhydride of 4-cinnamoyloxy-2-methyl-2H-1,2-benzothiazine-3-carboxylic acid 1,1-dioxide, m.p. 140°–142° C. If desired, the product is easily recrystallized for analytical purposes by dissolving it in 5 volumes of methylene chloride and slowly adding the same volume of diethyl ether and stirring for 1–2 hours at low temperature.

The I.R. spectrum (nujol mull) shows absorption peaks attributable to vibrations of alpha, beta-conjugated carbonyls at 1783 and 1738 cm$^{-1}$ (anhydride) and 1722 cm$^{-1}$ (ester group).

Analysis for $C_{28}H_{21}NO_7S$: calc. %: C 65.23, H 4.11, N 2.72, S 6.22, found %: C 64.96, H 4.13, N 2.70, S 6.18.

EXAMPLE 13

Mixed anhydrides of 4-hydroxy-2-methyl-2H-1,2-benzothiazine-3-carboxylic acid 1,1-dioxide, obtained as in Example 11, are directly reacted in methylene chloride solution with an equimolar amount of cinnamoyl chloride and triethylamine. After 1 hour at room temperature and precipitation with diethyl ether the corresponding mixed anhydrides of 4-cinnamoyloxy-2-methyl-2H-1,2-benzothiazine-3-carboxylic acid 1,1-dioxide are obtained in high yields.

EXAMPLE 14

To a solution of 38.5 g (0.1 mole) of cinnamoyl anhydride of 4-hydroxy-2-methyl-2H-1,2-benzothiazine-3-carboxylic acid 1,1-dioxide in 350 ml of methylene chloride, obtained according to Example 10, 18.8 g (0.2 mole) of 2-aminopyridine are added dropwise under stirring and external cooling. The mixture is kept at room temperature for 1.5 hours, then it is evaporated at low temperature and 350 ml of diethyl ether are added causing formation of an abundant crystalline precipitate which is collected. After drying, 24.8 g (yield 75%) of 4-hydroxy-2-methyl-N-(2-pyridyl)-2H-1,2-benzothiazine-3-carboxamide 1,1-dioxide are obtained, identical, for its chemical and physical properties (I.R., NMR), with an authentic sample of piroxicam. M.p. 196°–198° C., without depressione in admixture with piroxicam.

EXAMPLE 15

Solutions in methylene chloride of mixed anhydrides of 4-hydroxy-2-methyl-2H-1,2-benzothiazine-3-carboxylic acid 1,1-dioxide, obtained as in Example 11, are directly treated, without previous recovery or purification, with two molar amounts of 2-aminopyridine with stirring and cooling at 5°–10° C. After 1.5 hours at about 20° C., the procedure of Example 14 is followed obtaining in all cases the desired 4-hydroxy-2-methyl-N-(2-pyridyl)-2H-1,2-benzothiazine-3-carboxamide 1,1-dioxide with overall yield 60–70%.

EXAMPLE 16

A suspension of 30.9 g (0.06 mole) of cinnamoyl anhydride of 4-cinnamoyloxy-2-methyl-2H-1,2-benzothiazine-3-carboxylic acid 1,1-dioxide, obtained according to Example 12, in 300 ml of methylene chloride and 900 ml of diethyl ether is cooled 15° C. and treated, by quick dropping and with stirring, with 11.3 g (0.12 mole) of 2-aminopyridine.

The mixture is then stirred for 3 hours at 15° C., and an apparent change of crystalline appearance of the solid is observed.

The precipitate is then collected, washed thoroughly with a mixture methylene chloride: diethyl ether 1:4 and dried in vacuo. Yield 14.4 g (52%) of 4-cinnamoyloxy-2-methyl-N-(2-pyridyl)-2H-1,2-benzothiazine-3-carboxamide 1,1-dioxide as a colorless crystalline solid, m.p. 156°–158° C. with no depression when admised with an authentic sample.

EXAMPLE 17

The cinnamoyl anhydride and the other mixed anhydrides of 4-cinnamoyloxy-2-methyl-2H-1,2-benzothiazine-3-carboxylic acid 1,1-dioxide prepared respectively according to Example 12 or Example 13 are directly reacted, without previous purification or recovery from their methylene chloride solution, with 2–2.5 molar equivalents of 2-aminopyridine with stirring and external cooling. After dilution with 3 volumes of diethyl ether the reaction mixture is stirred at 15° C. for 3 hours, then the procedure of Example 16 is repeated obtaining the desired 4-cinnamoyloxy-2-methyl-N-(2-pyridyl)-2H-1,2-benzothiazine-3-carboxamide 1,1-dioxide.

What is claimed is:

1. A process for preparing derivatives of 2-methyl-N-(2-pyridyl)-2H-1,2-benzothiazine-3-carboxamide 1,1-dioxide of the formula:

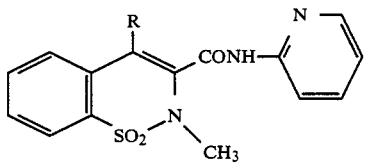

wherein R represents OH or a $OR_1$ group in which $R_1$ is cinnamoyl, which comprises reacting a strong base salt of 4-hydroxy-2-methyl-2H-1,2-benzothiazine-3-carboxylic acid 1,1-dioxide with cinnamoyl chloride, to give the corresponding anhydride which is unesterified or esterified at position 4; and reacting the obtained anhydride with 2-aminopyridine.

2. The process as in claim 1, in which cinnamoyl chloride is used in an essentially equimolar ratio.

3. A process for preparing 4-cinnamoyloxy-2-methyl-N-(2-pyridyl)-2H-1,2-benzothiazine-3-carboxamide 1,1-dioxide of the formula:

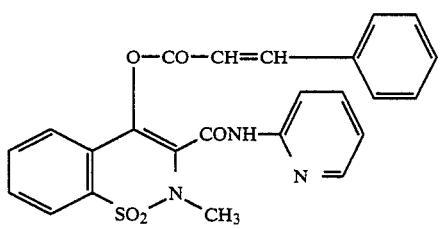

which comprises reacting a strong base salt of 4-hydroxy-2-methyl-2H-1,2-benzothiazine-3-carboxylic acid 1,1-dioxide with at least 2 molar ratios of cinnamoyl chloride to give the corresponding mixed anhydride esterified at position 4, and reacting said mixed anhydride with 2-aminopyridine.

4. The process as in claim 1, in which the reaction with cinnamoyl chloride is carried out in an inert organic solvent at a temperature between 0° C. and the boiling temperature of the solvent.

5. The process as in claim 1, in which the reaction with 2-aminopyridine is carried out in an inert solvent or solvent mixture at a temperature between 0° and 40° C.

6. The process as in claim 1, in which the salt of 4-hydroxy-2-methyl-2H-1,2-benzothiazine-3-carboxylic acid 1,1-dioxide is a monobasic (carboxylate) or dibasic (carboxylate-enolate) salt.

7. The process as in claim 1, in which the strong base is selected from the group ocnsisting of sodium hydroxide, potassium hydroxide and triethylamine.

8. The process as in claim 4 or claim 5, in which the inert solvent is methylene chloride.

9. The process as in claim 1, in which the preparation of the mixed anhydride and the esterification at position 4 are carried out in a single step.

10. The process as in claim 1, in which the preparation of the mixed anhydride and the subsequent reaction with 2-aminopyridine are carried out in a single step.

11. The process as in claim 5, in which the solvent mixture of the final reaction is a 1:3 mixture of methylene chloride:diethyl ether.

12. The process as in claim 11 in which the reaction temperature is 15°–20° C.

13. A compound of the formula:

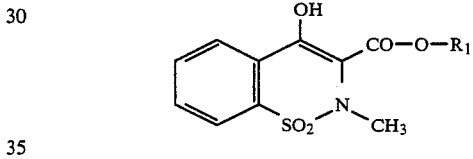

being an anhydride of 4-hydroxy-2-methyl-2H-1,2-benzothiazine-3-carboxylic acid 1,1-dioxide, in which $R_1$ represents cinnamoyl.

14. A compound of the formula:

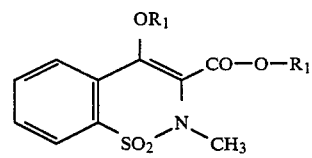

being a mixed anhydride of 4-cinnamoyloxy-2-methyl-2H-1,2-benzothiazine-3-carboxylic acid 1,1-dioxide, in which $R_1$ represents cinnamoyl.

* * * * *